(12) United States Patent
Li et al.

(10) Patent No.: US 11,033,032 B2
(45) Date of Patent: Jun. 15, 2021

(54) **LECLERCIA ADECARBOXYLATA BIOCONTROL STRAIN EFFICIENTLY INHIBITING PRODUCTION OF AFLATOXINS BY *ASPERGILLUS FLAVUS* AND APPLICATION THEREOF**

(71) Applicant: OIL CROPS RESEARCH INSTITUTE, CHINESE ACADEMY OF AGRICULTURAL SCIENCES, Wuhan (CN)

(72) Inventors: Peiwu Li, Wuhan (CN); Xiaoxia Ding, Wuhan (CN); Yizhen Bai, Wuhan (CN); Wen Zhang, Wuhan (CN); Qi Zhang, Wuhan (CN)

(73) Assignee: OIL CROPS RESEARCH INSTITUTE, CHINESE ACADEMY OF AGRICULTURAL SCIENCES, Hubei (CN)

( * ) Notice: Subject to any disclaimer, the term of this patent is extended or adjusted under 35 U.S.C. 154(b) by 41 days.

(21) Appl. No.: 16/204,654

(22) Filed: Nov. 29, 2018

(65) Prior Publication Data

US 2019/0159461 A1 May 30, 2019

(30) Foreign Application Priority Data

Nov. 29, 2017 (CN) .......................... 201711228608.X

(51) Int. Cl.
*A01N 63/00* (2020.01)
*C12N 1/20* (2006.01)
*C12R 1/01* (2006.01)

(52) U.S. Cl.
CPC .............. *A01N 63/00* (2013.01); *C12N 1/20* (2013.01); *C12R 1/01* (2013.01)

(58) Field of Classification Search
None
See application file for complete search history.

(56) References Cited

U.S. PATENT DOCUMENTS 6,823,623 B2 * 11/2004 Minato .................... A01C 1/08
47/57.6

OTHER PUBLICATIONS

Kai Wang et al. "Diversity of culturable root-associated/endophytic bacteria and their chitinolytic and aflatoxin inhibition activity of peanut plant in China". World J Microbiol Biotechnol. 2013, 29:1-10.*
Kazumichi Tamura et al. "Leclercia adecarboxylata gen non., comb. Nov., formerly known as *Escherichia* carboxylate". Current Microbiology 1986, vol. 13, pp. 179-184.*

* cited by examiner

*Primary Examiner* — Vera Afremova
(74) *Attorney, Agent, or Firm* — Hamre, Schumann, Mueller & Larson, P.C.

(57) ABSTRACT

The present invention relates to the microbiological field, and particularly relates to a *Leclercia* adcarboxglata biocontrol strain efficiently inhibiting production of aflatoxins by *Aspergillus flavus*. The *Leclercia* adcarboxglata biocontrol strain Wt16 was deposited at China Center for Type Culture Collection (CCTCC) on Jun. 13, 2017, and the accession number of the strain is CCTCC No. M2017331. The *Leclercia* adcarboxglata strain Wt16 is isolated from peanut pods for the first time which can significantly inhibit aflatoxins production by *Aspergillus flavus*, and also has an extremely good effect on inhibiting aflatoxins production by *Aspergillus flavus* for peanuts from different sources.

3 Claims, 1 Drawing Sheet

Figure 1:
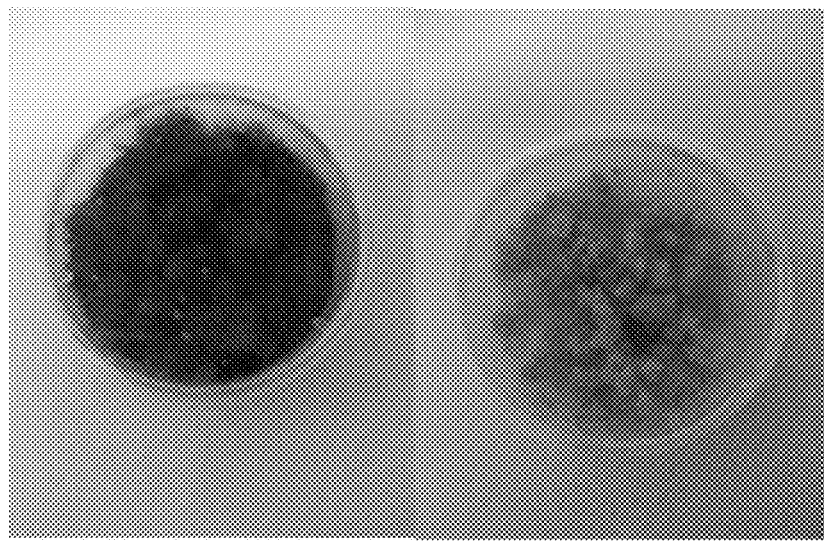

Specification includes a Sequence Listing.

SEQUENCE LISTING

```
<160> NUMBER OF SEQ ID NOS: 1

<210> SEQ ID NO 1
<211> LENGTH: 1455
<212> TYPE: DNA
<213> ORGANISM: Leclercia adcarboxglata

<400> SEQUENCE: 1
agggccctcc cgaaggttaa gctacctact tcttttgcaa cccactccca tggtgtgacg      60
ggcggtgtgt acaaggcccg ggaacgtatt caccgtagca ttctgatcta cgattactag     120
cgattccgac ttcatggagt cgagttgcag actccaatcc ggactacgac gcactttatg     180
aggtccgctt gctctcgcga gttcgcttct ctttgtatgc gccattgtag cacgtgtgta     240
gccctactcg taagggccat gatgacttga cgtcatcccc accttcctcc agtttatcac     300
tggcagtctc ctttgagttc ccggccggac cgctggcaac aaaggataag ggttgcgctc     360
gttgcgggac ttaacccaac atttcacaac acgagctgac gacagccatg cagcacctgt     420
ctcagagttc ccgaaggcac caatccatct ctggaaagtt ctctggatgt caagagtagg     480
taaggttctt cgcgttgcat cgaattaaac cacatgctcc accgcttgtg cgggcccccg     540
tcaattcatt tgagttttaa ccttgcggcc gtactcccca ggcggtcgac ttaacgcgtt     600
agctccggaa gccacgcctc aagggcacaa cctccaagtc gacatcgttt acggcgtgga     660
ctaccagggt atctaatcct gtttgctccc cacgctttcg cacctgagcg tcagtctttg     720
tcaggggggc cgccttcgcc accggtattc ctccagatct ctacgcattt caccgctaca     780
cctggaattc taccccctc tacaagactc tagcctgcca gtttcgaatg cagttcccag     840
```

-continued

```
gttgagcccg gggatttcac atccgacttg acagaccgcc tgcgtgcgct ttacgcccag    900
taattccgat taacgcttgc accctccgta ttaccgcggc tgctggcacg gagttagccg    960
gtgcttcttc tgcgggtaac gtcaattgct gcggttatta accacaacac cttcctcccc   1020
gctgaaagta ctttacaacc cgaaggcctt cttcatacac gcggcatggc tgcatcaggc   1080
ttgcgcccat tgtgcaatat tccccactgc tgcctcccgt aggagtctgg accgtgtctc   1140
agttccagtg tggctggtca tcctctcaga ccagctaggg atcgtcgcct aggtgagccg   1200
ttaccccacc tactagctaa tcccatctgg gcacatctga tggcaagagg cccgaaggtc   1260
cccctctttg gtcttgcgac gttatgcggt attagctacc gtttccagta gttatccccc   1320
tccatcaggc agtttcccag acattactca cccgtccgcc actcgtcacc cgagagcaag   1380
ctctctgtgc taccgttcga cttgcatgtg ttaggcctgc cgccagcgtt caatctgagc   1440
caggatcaaa ctcta                                                    1455
```

LECLERCIA ADECARBOXYLATA BIOCONTROL STRAIN EFFICIENTLY INHIBITING PRODUCTION OF AFLATOXINS BY ASPERGILLUS FLAVUS AND APPLICATION THEREOF

CROSS-REFERENCE TO RELATED APPLICATION

This application claims the benefit of China application serial No. 201711228608.X, filed on Nov. 29, 2017. The entirety of the above-mentioned patent application is hereby incorporated by reference herein and made a part of this specification.

FIELD

The present invention belongs to the microbiological field, and particularly relates to a Leclercia adcarboxglata biocontrol strain efficiently inhibiting production of aflatoxins by Aspergillus flavus and an application thereof.

BACKGROUND

Aspergillus flavus is a pathogenic fungus capable of producing powerful carcinogenic and highly toxic mycotoxins aflatoxins. Aflatoxins include families B, G and M, wherein B1 is the most common and most toxic. The aflatoxins can pollute grain crops such as peanuts and corn extensively, seriously threatening the health of human and livestock, and causing a huge economic loss. Therefore, it is urgent to strengthen prevention and control of Aspergillus flavus and toxin pollution.

Currently, there are three methods of prevention and control of Aspergillus flavus, namely, physical, chemical and biological control methods. However, chemical control is expensive and is likely to cause environmental pollution. In addition, while chemical control is adopted for controlling pathogenic bacteria, the pathogenic bacteria are prone to drug tolerance and even drug resistance to chemical agents. Physical control is time-consuming and labour-intensive, and its toxin-removing rate is not high, and it easily causes nutrient loss. Biological control has advantages of being safe, efficient and durable. Therefore, it is of great significance to strengthen the research on the biological prevention and control of Aspergillus flavus for China's agricultural industry and economic benefits.

The Leclercia adcarboxglata is rarely isolated from environmental and clinical specimens. According to current reports, the Leclercia adcarboxglata is generally isolated from blood, wound secretions, gallbladder tissues, a peritoneal dialysis solution, and urine. Moreover, reports have not been seen in the existing research regarding use of Leclercia adcarboxglata for inhibiting production of aflatoxins by Aspergillus flavus.

SUMMARY OF THE INVENTION

The present invention provides a Leclercia adcarboxglata biocontrol strain which can efficiently inhibit production of aflatoxins by Aspergillus flavus and an application thereof. In an embodiment, the Leclercia adcarboxglata biocontrol strain Wt16 is provided, which was deposited at China Center for Type Culture Collection (CCTCC) on Jun. 13, 2017. The deposition address is Wuhan University, Wuhan, China, and the accession number of the strain is CCTCC No. M2017331.

According to the present invention, the Leclercia adcarboxglata strain capable of inhibiting aflatoxins production by Aspergillus flavus was isolated from peanut pods for the first time. A screening method comprises the following steps: washing the peanut pods picked from a peanut field in Huangpi of Hubei Province with tap water, placing the washed peanut pods in an LB solid medium for culture, picking growing bacteria with an inoculating loop, transferring the picked bacteria to a fresh LB solid medium for plate streaking, picking a single colony after transferring for several times, and performing co-culture tests on the picked single colony and Aspergillus flavus in a medium (namely performing co-culture antibacterial tests by in vitro inoculation of peanuts with the Aspergillus flavus) to measure toxin productivity; and finally screening a Leclercia adcarboxglata biocontrol strain Wt16 capable of remarkably inhibiting Aspergillus flavus from generating toxins. The strain was deposited at China Center for Type Culture Collection (CCTCC) with an accession number of CCTCC No. M2017331.

The strain is identified with a 16S rDNA specific amplification technique, morphological characteristics, and physiological and biochemical tests. The results show that the strain is a Leclercia adcarboxglata strain belonging to enterobacteriaceae, and is also a unique strain of Leclercia adcarboxglata genus. The 16S rRNA sequence of the Leclercia adcarboxglata biocontrol strain Wt16 is as shown in SEQ ID NO.1.

TABLE 1

Major biological characteristics of leclercia adcarboxglata Wt16:

| Gram staining | Oxygen | Spore | Capsule | Nutrient requirements | Culture temperature | Culture time | V.P test | M.R test | Oxidase | Cellulose degradation | Nitrate reduction |
|---|---|---|---|---|---|---|---|---|---|---|---|
| Negative | Facultative anaerobic | No | No | Low | 25-37° C. | 12-24 h | Negative | Negative | Negative | Negative | Positive |

In an embodiment, an inhibitor for aflatoxins production by Aspergillus flavus is provided which comprises biologically pure culture of the Leclercia adcarboxglata biocontrol strain Wt16.

In an embodiment, the inhibitor is in a form of a liquid, a dust, a dry wettable powder or a dry wettable granule.

In an embodiment, the inhibitor is in a form of a liquid and the Leclercia adcarboxglata biocontrol strain Wt16 is present at a concentration of $(1-9) \times 10^7$ CFU/mL.

In an embodiment, the inhibitor is a fermentation liquid of the Leclercia adcarboxglata biocontrol strain Wt16. A preparation method of the fermentation liquid comprises the following steps: activating the Leclercia adcarboxglata strain Wt16 in an LB plate, performing culturing in an incubator at 25-37° C. for 24 h, picking a single colony of Leclercia adcarboxglata with a teasing needle, transferring the single colony to a liquid medium for shaking culture for 12-24 h, sucking 1-3% of a culture solution, and transferring the culture solution to a fresh liquid medium for shaking culture for 12-24 h, so as to obtain the antagonistic *Leclercia adcarboxglata* strain Wt16 fermentation liquid.

In an embodiment, a method of preparing the inhibitor is provided, the method comprising:
   activating the *Leclercia* adcarboxglata strain Wt16 in an LB plate,
   performing culturing in an incubator at 25-37° C. for 24 h,
   picking a single colony of *Leclercia* adcarboxglata with a teasing needle,
   transferring the single colony to a liquid medium for shaking culture for 12-24 h,
   sucking 1-3% of a culture solution, and
   transferring the culture solution to a fresh liquid medium for shaking culture for 12-24 h, so as to obtain an antagonistic *Leclercia* adcarboxglata strain Wt16 fermentation liquid.

In an embodiment, an application of the inhibitor for inhibiting the production of aflatoxins by *Aspergillus flavus* is provided. The specific method is as follows: coating surfaces of a biological sample with the inhibitor or mixing the inhibitor with a biological sample to inhibit the production of aflatoxins by *Aspergillus flavus*, so as to prevent the biological sample from aflatoxin pollution.

In an embodiment, an application of the *Leclercia* adcarboxglata strain Wt16 for inhibiting the production of aflatoxins by *Aspergillus flavus* is provided. The specific method is as follows: coating surfaces of a biological sample with a fermentation liquid of the *Leclercia* adcarboxglata strain Wt16 or mixing a fermentation liquid of the *Leclercia* adcarboxglata strain Wt16 with the biological sample to inhibit the production of aflatoxins by *Aspergillus flavus*, so as to prevent the biological sample from aflatoxin pollution.

The *Leclercia* adcarboxglata strain Wt16 which has a good effect on controlling *Aspergillus flavus* is isolated from peanut pods for the first time. The strain can significantly inhibit aflatoxins production by *Aspergillus flavus*, and also has an extremely good effect on inhibiting aflatoxins production by *Aspergillus flavus* for peanuts from different sources.

BRIEF DESCRIPTION OF THE DRAWINGS

FIG. 1 shows growth conditions of the inoculated peanut powder in embodiment 2. The left picture shows the growth condition of the peanut powder inoculated with the *Aspergillus flavus* and then cultured for 9 days by using a Sabourand liquid medium as a control; and the right picture shows the growth condition of the peanut powder inoculated simultaneously with the *Leclercia* adcarboxglata strain Wt16 and the *Aspergillus flavus* and then cultured for 9 days.

FIG. 2 shows growth conditions of the peanut kernels before and after inoculation in embodiment 3. The left picture shows the growth condition of the peanuts inoculated simultaneously with the *Leclercia* adcarboxglata strain Wt16 and the *Aspergillus flavus* and then cultured for 9 days; and the right picture shows the growth condition of the peanuts inoculated with *Aspergillus flavus* and then cultured for 9 days by using a Sabourand liquid medium as a control.

DETAILED DESCRIPTION

The method comprises the following steps: washing peanut pods picked from a peanut field in Huangpi of Hubei Province with tap water, placing the washed peanut pods in an LB solid medium for culture, picking growing bacteria with an inoculating loop, transferring the picked bacteria to a fresh LB solid medium for plate streaking, picking a single colony after transferring for several times, and performing co-culture tests on the picked single colony and *Aspergillus flavus* in a medium to measure toxin productivity, namely performing co-culture antibacterial tests by in vitro inoculation of peanuts with the *Aspergillus flavus*; and finally screening a *Leclercia* adcarboxglata biocontrol strain Wt16 capable of remarkably inhibiting the production of aflatoxins by *Aspergillus flavus*. The strain was deposited at China Center for Type Culture Collection (CCTCC) with an accession number of CCTCC No. M2017331.

Embodiment 1

1) activating the *Leclercia* adcarboxglata strain Wt16 in an LB plate, performing culturing in an incubator at 37° C. for 24 h, picking a single colony of *Leclercia* adcarboxglata with a teasing needle, transferring the single colony to a triangular flask with 15 mL of LB liquid medium, and performing shaking culture at 28° C. and at 200 $r \cdot min^{-1}$ for 12 h; and sucking 1% of a culture solution, transferring the culture solution to a triangular flask with 15 mL of LB liquid medium, and performing shaking culture at 28° C. and at 200 $r \cdot min^{-1}$ for 12 h, so as to obtain an antagonistic strain fermentation liquid;

2) culturing the *Leclercia* adcarboxglata fermentation liquid (final concentration is $1 \times 10^7$ CFU/mL) and thriving *Aspergillus flavus* suspension after 7 days of culture (final spore concentration is $5.0 \times 10^5$ spores $mL^{-1}$) together in a Sabourand liquid medium at 28° C. and at 200 rpm for 5 days, wherein each treatment is repeated for 3 times; and 3) measuring the content of aflatoxin B1 in the culture solution (Table 2).

TABLE 2

Control effect of biocontrol bacteria on *aspergillus flavus*

| Treatment | *A. flavus* | *A. flavus* + CCTCC No. M 2017331 |
|---|---|---|
| Content of AFB1 (ng/ml) | 215.22 ± 36.59 | 0.8167 ± 0.09518 |

As can be seen from the test result, the *Leclercia* adcarboxglata strain CCTCC No. M2017331 has an aflatoxin inhibiting rate of 99.6%, showing that the strain has the capacity of inhibiting aflatoxin production.

Embodiment 2

1) grinding "Zhonghua No. 6" peanut kernels taken from a peanut field of Hubei Province into powder, weighing and placing 1 g of the peanut powder to a culture dish, and at the same time adding 1 mL of *Aspergillus flavus* spore suspension ($5 \times 10^5$/mL) and 1 mL of CCTCC M2017331 bacterial liquid ($1 \times 10^7$ CFU/mL). A Sabourand medium is used for replacing the CCTCC M2017331 fermentation liquid as a control;

2) culturing the inoculated peanut powder in an incubator at 28° C. for 9 days, observing the growth condition (FIG. 1), then adding 15 mL of 70% aqueous methanol to obtain a mixture, and placing the mixture into a shaker for 30 min after being mixed in a vortex manner; taking 3 mL of supernatant, adding 8 mL of ultrapure water and performing vortex centrifugation;

3) taking 8 mL of supernatant, and measuring the content of aflatoxin B1 (Table 3) by an immunoaffinity column- HPLC method. 3 repeats are set in the test. The left picture of FIG. 1 shows the growth condition of the peanut powder inoculated with the *Aspergillus flavus* and then cultured for 9 days by using a Sabourand liquid medium as a control; and the right picture shows the growth condition of the peanut powder inoculated simultaneously with the *Leclercia* adcarboxglata strain Wt16 and the *Aspergillus flavus* and then cultured for 9 days.

TABLE 3

Control effect of biocontrol bacteria on peanut *aspergillus flavus*

| Treatment | A. flavus | A. flavus + CCTCC No. M 2017331 |
|---|---|---|
| Content of Toxins (ng/ml) | 516.61 ± 51.91 | 86.84 ± 14.13 |

As can be seen from the test result, the strain CCTCC M2017331 on the "Zhonghua No. 6" peanuts has an aflatoxin inhibiting rate of approximately 83%, showing that the strain has a good effect of controlling aflatoxins during the storage of peanuts.

Embodiment 3

Figure 2:

1) taking 10 "Luhua No. 8" peanut kernels from a peanut field of Anhui Province, coating the surfaces of the peanut kernels with the fermentation liquid of the *Leclercia adcarboxylata* strain Wt16 and at the same time adding 1 mL of *Aspergillus flavus* spore suspension (5×10$^5$/mL). A Sabourand medium is used for replacing the CCTCC M2017331 fermentation liquid as a control;

2) culturing the inoculated peanut kernels in an incubator at 28° C. for 9 days, observing the growth condition (FIG. 2), then grinding the peanut kernels into peanut powder, adding 15 mL of 70% aqueous methanol, and placing the mixture into a shaker for 30 min after being mixed in a vortex manner; and taking 3 mL of supernatant, adding 8 mL of ultrapure water, and performing vortex centrifugation. The left picture of FIG. 2 shows growth condition of the peanuts inoculated simultaneously with the *Leclercia* adcarboxglata strain Wt16 and the *Aspergillus flavus* and then cultured for 9 days; and the right picture shows the growth condition of the peanuts inoculated with *Aspergillus flavus* and then cultured for 9 days by using a Sabourand liquid medium as a control;

3) taking 8 mL of supernatant, and measuring the content of aflatoxin B1 (Table 4) by an immunoaffinity column-HPLC method. 3 repeats are set in the test.

TABLE 4

Control effect of biocontrol bacteria on peanut *aspergillus flavus*

| Treatment | A. flavus | A. flavus + CCTCC No. M 2017331 |
|---|---|---|
| Content of Toxins (ng/ml) | 449.95 ± 42.51 | 51.74 ± 3.30 |

As can be seen from the test result, the strain CCTCC M2017331 on the "Luhua No. 8" peanuts has a rate of inhibiting the *Aspergillus flavus* from producing toxins being approximately 88.5%, showing that the strain has an extremely good biocontrol effect on peanuts of different kinds.

What is claimed is:

1. An inhibitor for inhibiting production of aflatoxins by *Aspergillus flavus*, wherein the inhibitor is a man-made fermentation liquid of the *Leclercia adecarboxylata* biocontrol strain Wt16, and the *Leclercia adecarboxylata* biocontrol strain Wt16 was deposited at China Center for Type Culture Collection (CCTCC) on Jun. 13, 2017 with the access number CCTCC No. M2017331, wherein the fermentation liquid is made by a preparation method comprising:

streaking the *Leclercia adecarboxylata* strain Wt16 on a Luria broth (LB) plate, and placing the LB plate in an incubator at 25-37° C. for 24 h, picking a single colony of *Leclercia adecarboxylata* with a teasing needle, transferring the single colony to a liquid medium and then shaking the liquid medium for 12-24 h to obtain a culture, and inoculating a portion of the culture to a fresh liquid medium and then shaking for 12-24 h, so as to obtain an antagonistic *Leclercia adecarboxylata* strain Wt16 fermentation liquid.

2. A method of inhibiting production of aflatoxins by *Aspergillus flavus*, comprising: coating surfaces of a biological sample containing *Aspergillus flavus* with an inhibitor for inhibiting production of aflatoxins by *Aspergillus flavus* or mixing the inhibitor with a biological sample containing *Aspergillus flavus* to inhibit the production of aflatoxins by *Aspergillus flavus,* the inhibitor comprises a man-made culture of the *Leclercia adecarboxylata* biocontrol strain Wt16 deposited at China Center for Type Culture Collection (CCTCC) on Jun. 13, 2017, with the access number CCTCC No. M2017331.

3. A method of preparing an inhibitor for inhibiting production of aflatoxins by *Aspergillus flavus*, comprising:

streaking the *Leclercia adecarboxylata* strain Wt16 on a Luria broth (LB) plate, placing the LB plate in an incubator at 25-37° C. for 24 h, picking a single colony of *Leclercia adecarboxylata* with a teasing needle, transferring the single colony to a liquid medium and then shaking for 12-24 h to obtain a culture, and inoculating a portion of the culture into a fresh liquid medium and then shaking for 12-24 h, so as to obtain a man-made antagonistic *Leclercia adecarboxylata* strain Wt16 fermentation liquid, wherein the *Leclercia adecarboxylata* biocontrol strain Wt16 was deposited at China Center for Type Culture Collection (CCTCC) on Jun. 13, 2017, with the access number CCTCC No. M2017331.

* * * * *